(12) United States Patent
Ljungmann et al.

(10) Patent No.: US 7,952,798 B2
(45) Date of Patent: May 31, 2011

(54) HOLDING DEVICE FOR MICROSCOPE SLIDES WITH TISSUE SPECIMENS

(75) Inventors: Øystein Ljungmann, Siggerud (NO); Torstein Ljungmann, Nesoddtangen (NO)

(73) Assignee: Dako Instrumec AS, Oslo (NO)

( * ) Notice: Subject to any disclaimer, the term of this patent is extended or adjusted under 35 U.S.C. 154(b) by 748 days.

(21) Appl. No.: 11/793,557

(22) PCT Filed: Dec. 22, 2005

(86) PCT No.: PCT/NO2005/000476
§ 371 (c)(1),
(2), (4) Date: Mar. 11, 2008

(87) PCT Pub. No.: WO2006/068502
PCT Pub. Date: Jun. 29, 2006

(65) Prior Publication Data
US 2009/0027770 A1    Jan. 29, 2009

(30) Foreign Application Priority Data
Dec. 23, 2004   (NO) .................................. 20045625

(51) Int. Cl.
*G02B 21/26* (2006.01)
(52) U.S. Cl. ....................................... 359/391; 356/244
(58) Field of Classification Search ........................ None
See application file for complete search history.

(56) References Cited

U.S. PATENT DOCUMENTS

| | | | |
|---|---|---|---|
| 5,023,187 A | 6/1991 | Koebler et al. | |
| 6,094,301 A | 7/2000 | Dreyer et al. | |
| 6,703,247 B1 | 3/2004 | Chu | |
| 2004/0002163 A1* | 1/2004 | Reinhardt et al. | 436/174 |
| 2004/0071605 A1 | 4/2004 | Coonan et al. | |
| 2004/0091395 A1* | 5/2004 | Ward et al. | 422/63 |
| 2009/0110597 A1* | 4/2009 | Ljungmann et al. | 422/62 |

FOREIGN PATENT DOCUMENTS

| | | |
|---|---|---|
| BE | 756873 A | 3/1971 |
| DE | 200 05 999 U | 9/2001 |
| EP | 0 414 405 A | 2/1991 |
| GB | 2 197 949 A | 6/1988 |

(Continued)

OTHER PUBLICATIONS

Supplemental search report issued by European Patent Office for corresponding European application 05826423.5 mailed Aug. 3, 2009.

*Primary Examiner* — Lee Fineman
(74) *Attorney, Agent, or Firm* — Frommer Lawrence & Haug LLP; Ronald R. Santucci

(57) ABSTRACT

A holding device for retaining a number of microscope slides with tissue specimens, wherein the surfaces of the slides in retained position are located in a common plane. The holding device has an elongated hanger with a clamp for releasably clamping the microscope slides in a hanging position with the surfaces of the slides in the common plane. The microscope slides are clamped at their upper end and are free to fall from their own weight from the hanger by release from the clamp. The clamp preferably is arranged to cooperate with a loading rack having a supporting surface for support of the microscope slides, in which the hanger can be introduced into the rack and the clamp can be actuated so that all microscope slides placed on the supporting surface are clamped in the holding device.

10 Claims, 6 Drawing Sheets

FOREIGN PATENT DOCUMENTS

| | | | |
|---|---|---|---|
| GB | 2197949 A | * | 6/1988 |
| JP | 02-150549 U | | 6/1990 |
| WO | WO 94/23326 | | 10/1994 |
| WO | WO 9423326 A1 | * | 10/1994 |
| WO | WO 2004/008106 | | 1/2004 |
| WO | WO 2006/068500 A | | 6/2006 |

* cited by examiner

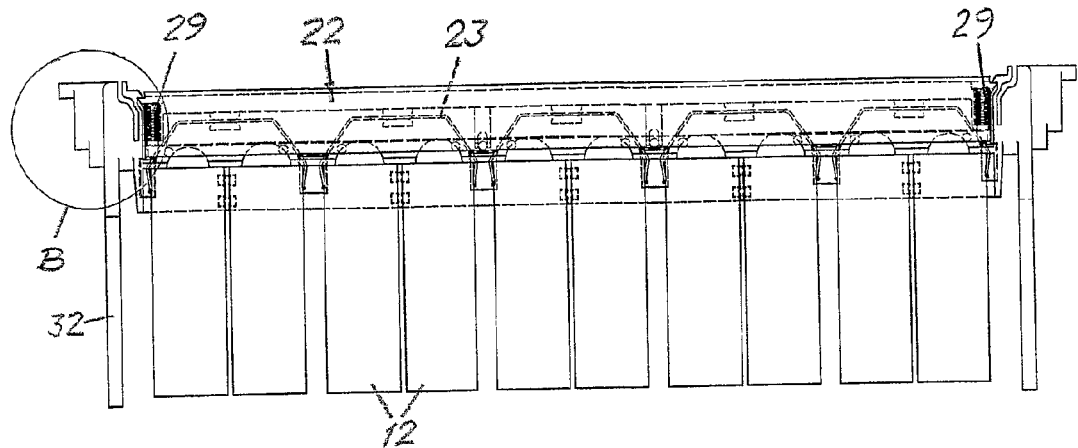
FIG. 6
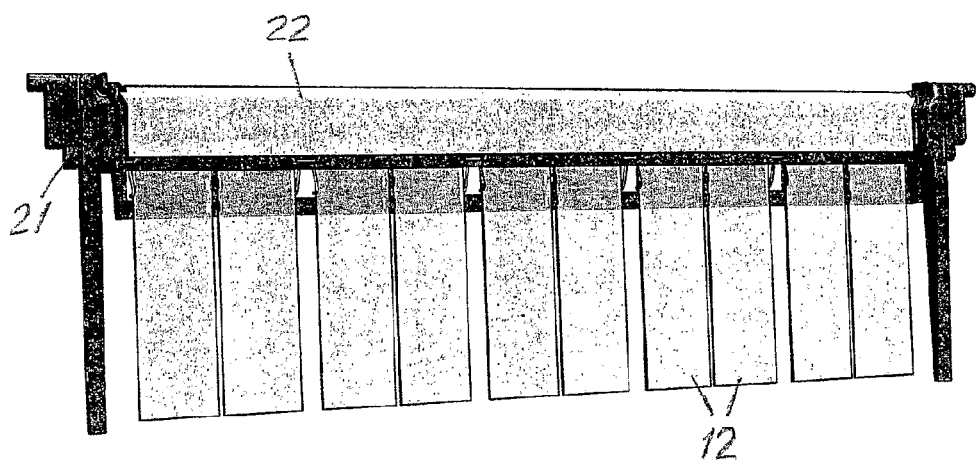
FIG. 8
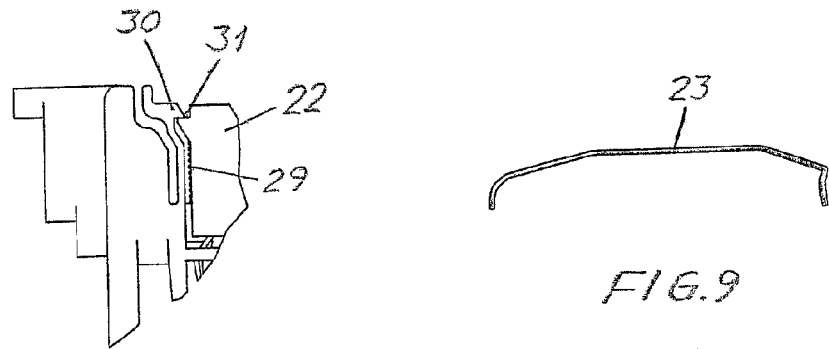
FIG. 7
FIG. 9

HOLDING DEVICE FOR MICROSCOPE SLIDES WITH TISSUE SPECIMENS

This is a 371 filing of International Patent Application No. PCT/NO2005/000476 filed Dec. 22, 2005 and published on Jun. 29, 2006 under publication number WO 2006/068502 A and claims priority benefits from Norwegian Patent Application No. 20045625 filed Dec. 23, 2004, the disclosure of which is hereby incorporated by reference.

The invention relates to a holding device for retaining a number of microscope slides with tissue specimens, wherein the surfaces of the microscope slides in retained position are located in a common plane.

A holding device of the above-mentioned type is known from WO 94/23326 (PCT/GB94/00671). The microscope slide holder according to this application comprises an essentially rectangular planar frame for receiving a number of microscope slides, wherein the frame is provided with a series of clamps for individual retention of the microscope slides in edge-to-edge relation, so that they cover a space essentially in the plane of the frame.

The purpose of the device is to provide a microscope slide holder enabling treatment of several microscope slides at the same time, to thereby achieve an efficient hybridization on site in connection with microscope examination of tissue specimens on the microscope slide. However, the arrangement with a frame surrounding the microscope slides, and a series of clamps for individual retention of the microscope slides, result in a construction which requires some effort with insertion into and withdrawal of the microscope slides from the frame, and which is not so simple and flexible as desirable.

It is an object of the invention to provide a holding device of the stated type which has a simple construction and which is flexible in that it e.g. allows the use of microscope slides with different dimensions.

Another object is to provide a holding device which can be used in an apparatus for staining of tissue specimens on microscope slides, and in an apparatus for placing of cover glasses on microscope slides, without manual handling of the microscope slides.

The above-mentioned objects are achieved with a holding device which, according to the invention, is characterised in that it comprises an elongated hanger having a clamping means for releasable clamping of microscope slides in a hanging position with the surfaces in said plane, the microscope slides being clamped at their upper end and by release from the clamping means being free to fall from the hanger because of their own weight.

An advantageous embodiment of the holding device is characterised in that the clamping means is arranged to cooperate with a loading rack having a supporting surface for the support of the current microscope slides in said plane, the hanger being able to be introduced in the rack so that the clamping means simultaneously clamps all microscope slides placed on the supporting surface.

The invention will be further described below in connection with exemplary embodiments with reference to the drawings, wherein FIG. 1 shows a plan view of a first embodiment of a holding device according to the invention;

FIG. 6 shows a plan view of the holding device in FIGS. 4 and 5, wherein a number of microscope slides are clamped in the holding device;

FIG. 7 shows the detail B in FIG. 6 on an enlarged scale;

FIG. 8 shows a perspective view of the holding device with clamped microscope slides;

FIG. 9 shows one of the clamping springs included in the holding device in FIGS. 4 and 5;

Figure 14:
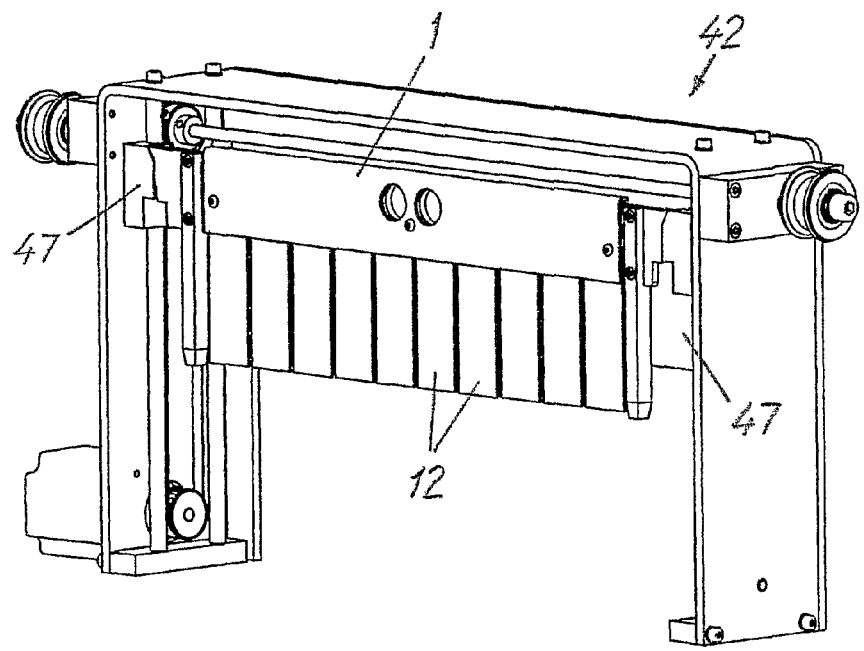
Figure 4:
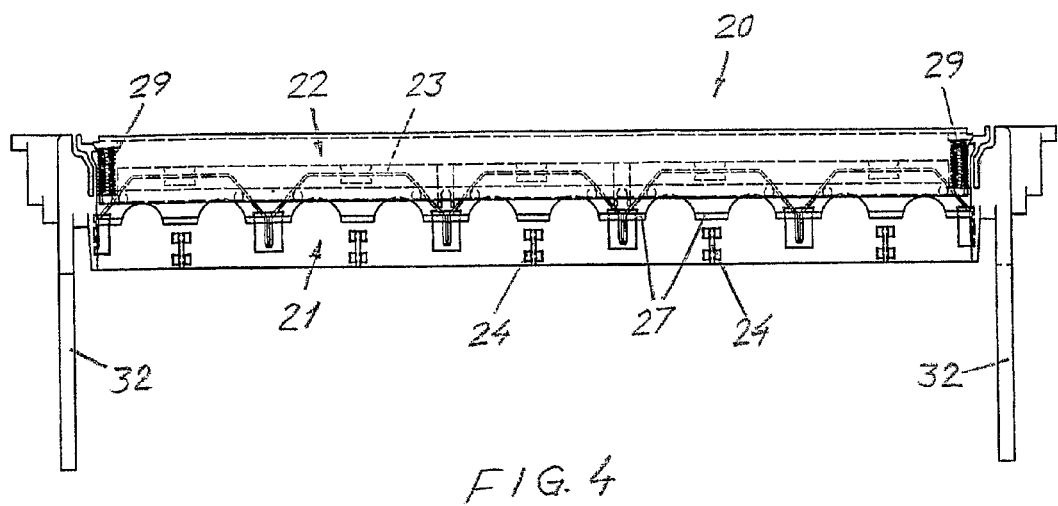
FIG. 4 shows a plan view of a second embodiment of a holding device according to the invention.
Figure 13:
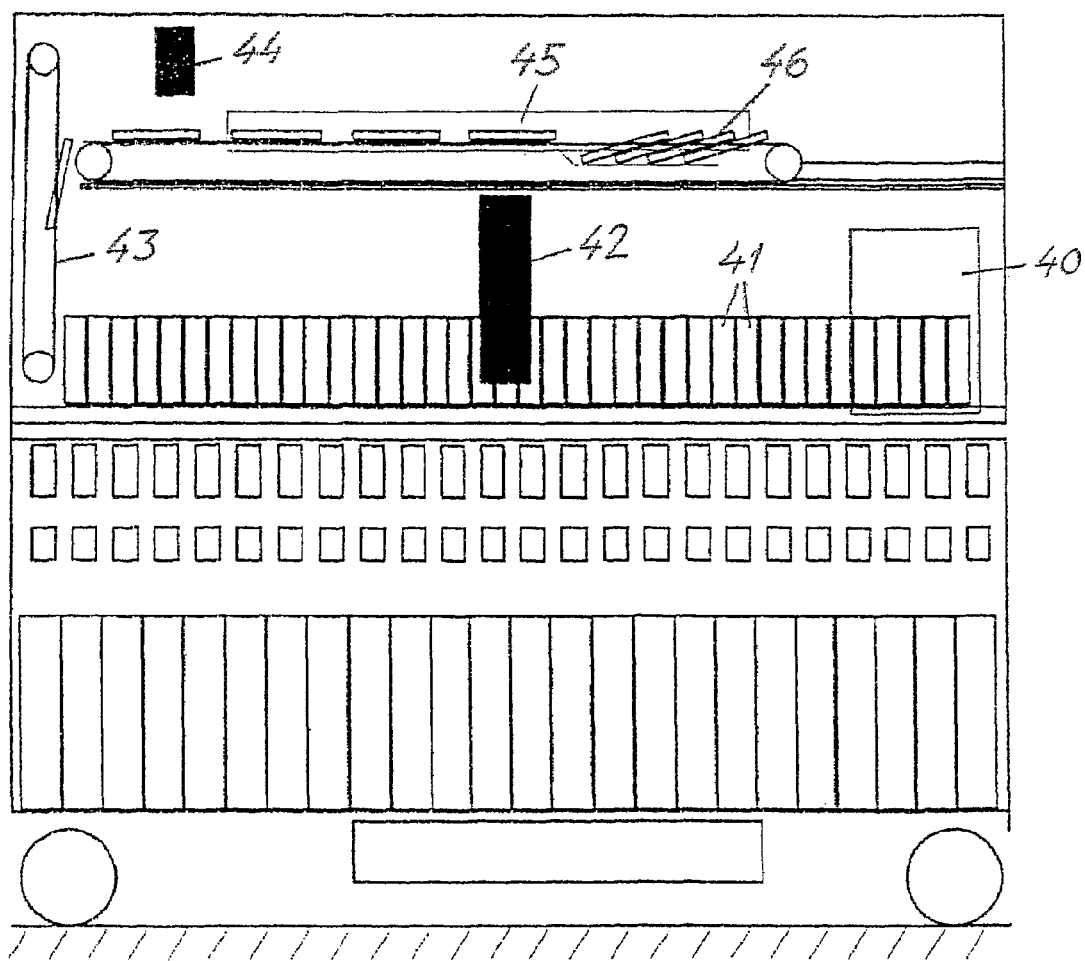

FIG. 13 shows a principle drawing of a multi-function apparatus for, inter alia, staining of tissue specimens on microscope slides and for placing of cover glasses on microscope slides, wherein the holding device according to the invention is applied; and FIG. 14 shows a perspective view of a conveyor for use in the apparatus in FIG. 4, wherein the holding device according to the invention with clamped microscope slides is placed in the conveyor.

Figure 1:
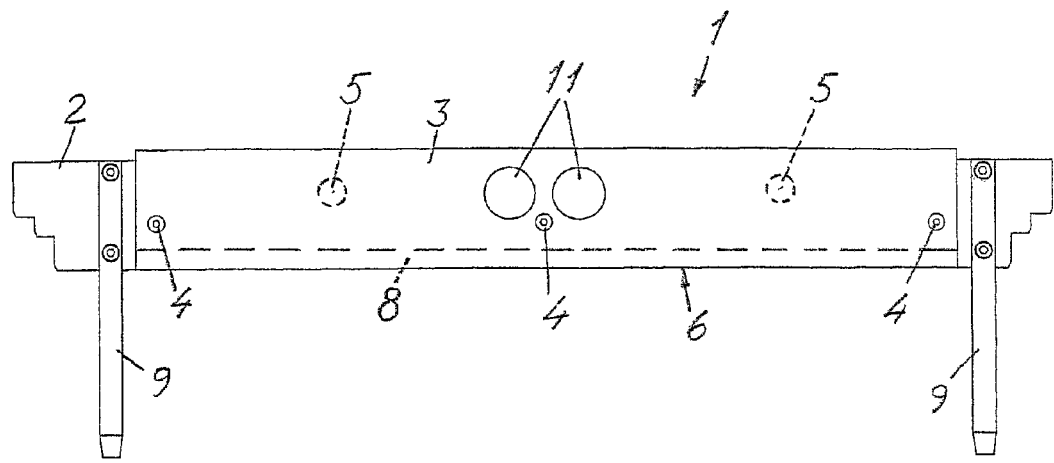

As shown in FIG. 1, the first embodiment of the holding device comprises an elongated hanger 1 consisting of a carrier plate 2 on which a clamp plate 3 adapted to the carrier plate is mounted by means of three pins 4 forming supporting points allowing a limited turning of the clamp plate about an axis of rotation extending through the supporting points. Between the carrier plate 2 and the clamp plate 3 there are placed two biasing springs 5 (shown stippled) affecting the clamp plate so that an edge portion thereof in cooperation with an edge portion of the carrier plate forms a clamping jaw 6 for clamping of microscope slides placed in a loading rack 7 (see FIG. 2). Along the clamping jaw the clamp plate 3 advantageously is provided with a resilient material (suggested at 8), e.g. a rubber strip, for resilient abutment against the relevant microscope slides that are to be clamped in the holding device.

A appears from FIG. 1, the carrier plate 2 of the hanger is also provided with a pair of projecting arms 9 for cooperation with corresponding guide members 10 at the ends of the loading rack 7, for guided introduction of the hanger 1 to a well-defined position in the loading rack. As shown, the hanger is also provided with a pair of gripping holes 11 for manual handling of the hanger.

Figure 2:
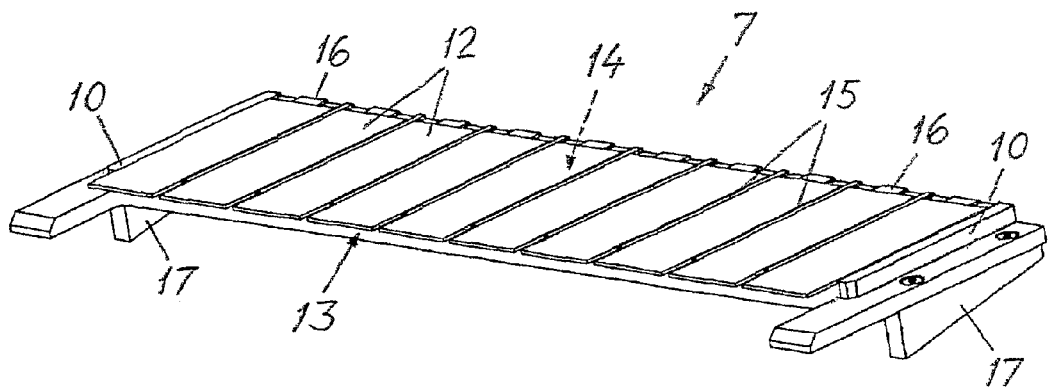
FIG. 2 shows a perspective view of a loading rack for use in connection with the holding means in FIG. 1.

FIG. 2 shows a perspective view of the loading rack 7 forming a loading station for microscope slides. As appears, the rack in the illustrated embodiment is dimensioned to receive ten microscope slides 12 of standard size. The rack comprises a main part 13 at the ends of which the guide members 10 for the hanger 1 are arranged. The main part forms a supporting surface 14 for the support of the microscope slides, so that these will be lying next to each other on the supporting surface in the same plane. On the supporting surface there are arranged dividing ribs 15 between the microscope slides, and the position of the microscope slides in the rack further is defined by an abutment edge formed by marking fields 16 for identification of the microscope slides.

The loading rack is supported by two foot members 17 having an inclined surface, so that the supporting surface 14 of the rack slants downwards towards the marking fields 16 when the rack is placed on a horizontal base. This contributes to a well-defined placing of the microscope slides in the rack.

Figure 3:
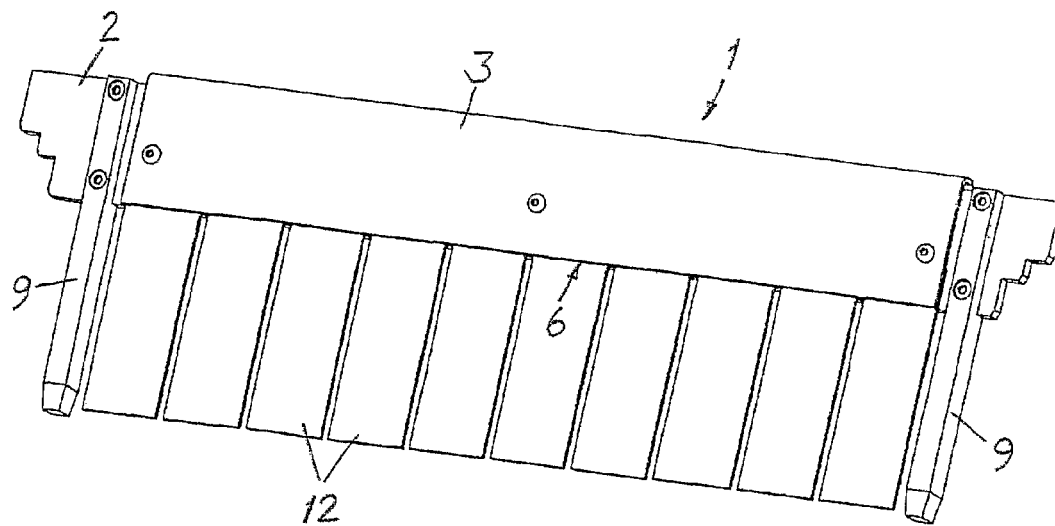
FIG. 3 shows a perspective view of the holding device in FIG. 1 with microscope slides clamped therein.

FIG. 3 shows the holding device 1 with microscope slides 12 clamped therein. The figure shows the microscope slides in their hanging position in the holding device, after this having been removed from the loading rack 7 with the microscope slides in clamped position.

Figure 5:
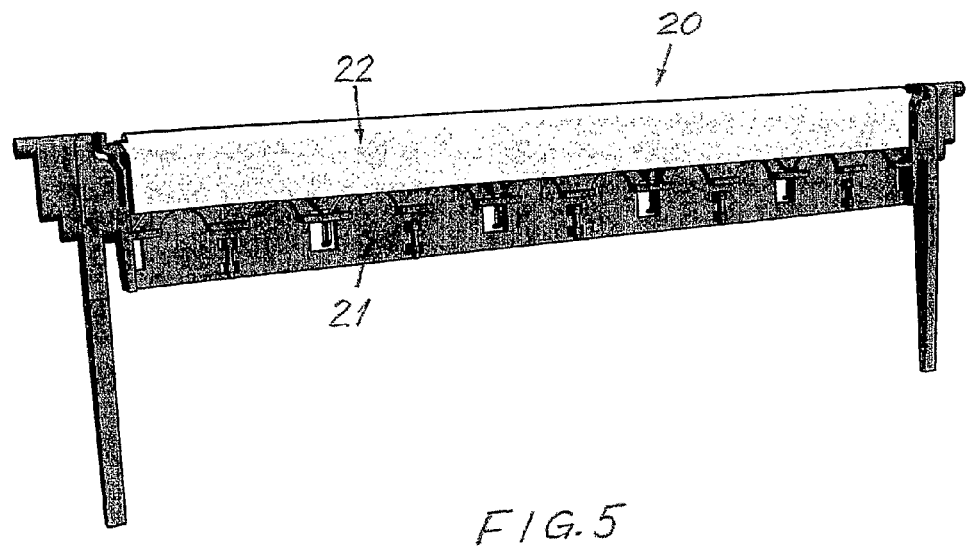
FIG. 5 shows a perspective view of the holding device in FIG. 4.

A second embodiment of the holding device according to the invention is shown in FIGS. 4 and 5. The holding device in its entirety is designated by the reference numeral 20 and includes a hanger 21 and an actuating means 22 for actuating a number of clamping springs 23 (5 in the illustrated case) mounted on the hanger 21 and constituting the clamping means thereof. The clamping springs provide for individual clamping of the respective microscope slides 12 (see FIG. 6). As appears, the actuating means 22 consists of an elongated locking/release profile (also 22) that can be moved between a first or inner position in the hanger (see FIG. 6) in which the clamping springs 23 are released so that they clamp respective pairs of microscope slides 12, and a second or outer position (see FIG. 4) in which the clamping springs are moved to an open position in which the microscope slides are released.

As appears from FIGS. 4 and 9, each of the clamping springs 23 consists of an approximately U-shaped spring wire element wherein the ends of the spring legs are adapted to actuate a respective pair of microscope slides 12, so that these are clamped against an intermediate abutment member 24 on the hanger.

Figure 10:
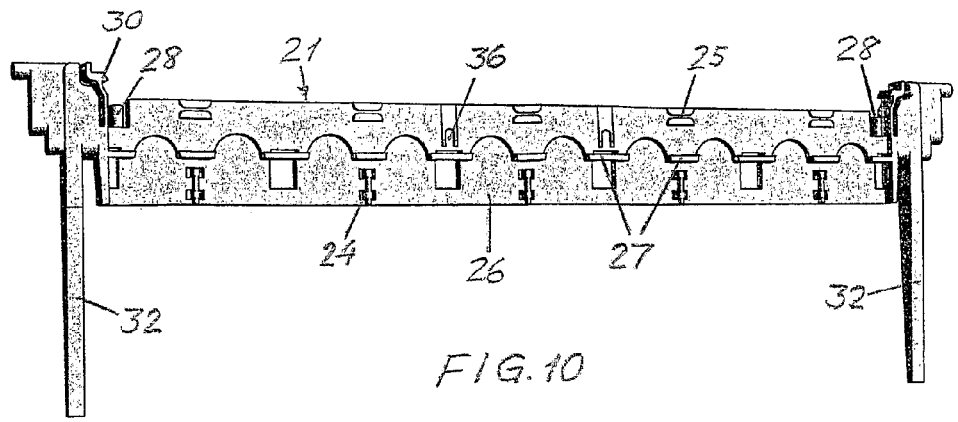
FIG. 10 shows a plan view of the hanger included in the holding device.
Figure 11:
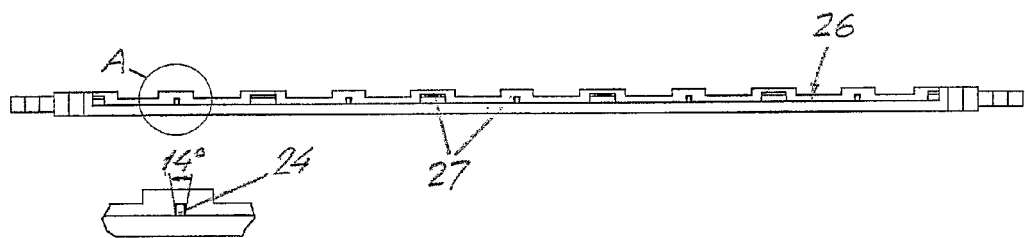
FIG. 11 shows the hanger in FIG. 10 as viewed from below, and an enlarged view of the detail A in the figure.
Figure 12:
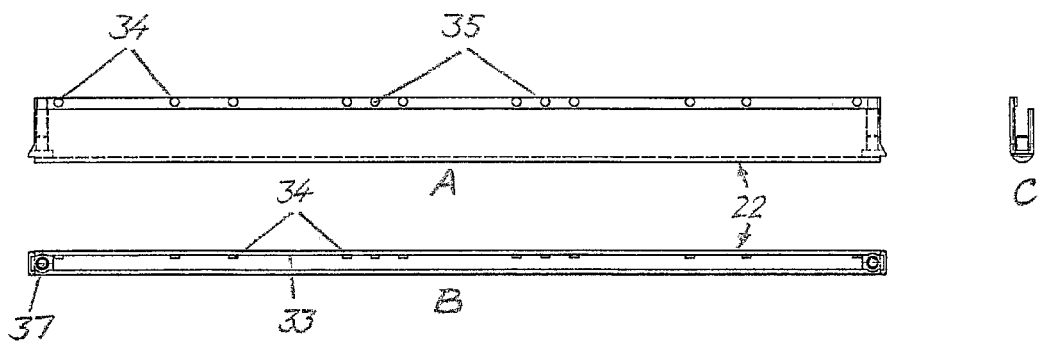
FIGS. 12A, B, C and D show a side view, a plan view, and an end view and a prospected view, respectively, of the locking/release profile included in the holding device.
Figure 12:
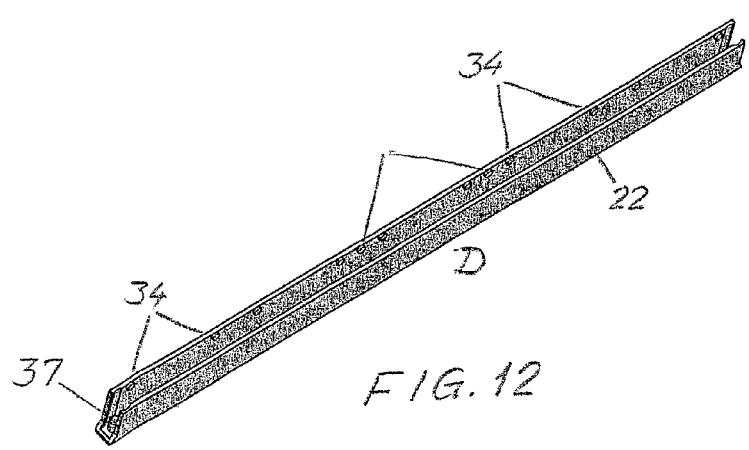

The design of the hanger 21 is further shown in FIGS. 10 and 11. Along on longitudinal side the hanger is provided with guide grooves 25 for mounting of the clamping springs 23. Said abutment members 24 for the microscope slides are arranged along the other longitudinal side of the hanger. The abutment members have sidewalls inclined upwards and outwards towards the respective microscope slide 12, so that the microscope slide in clamped position is pressed against the common plan 26 of the hanger 21. The inclined position of the sidewalls is shown in the enlarged detail A in FIG. 11. The angle of inclination suitably is ca. 7°.

As suggested in FIG. 9, also the ends of the legs of the clamping springs 23 are inclined in the direction outwards from the respective microscope slides, so that the springs in the clamping position as is in pressing the microscope slides downwards towards the common plan 26 of the hanger 21. Thereby directional stability is achieved for the microscope slides in the clamped position. The angle of inclination also here suitable is ca. 7°.

In its central region the hanger 21 is provided with a number of longitudinally extending abutment members 27 against which the end edges of the microscope slides rest when they are clamped in the hanger. At its ends the hanger is provided with a pair of guide pins 28 on which there are placed a pair of helical springs 29 (see FIGS. 4 and 6) the function of which is to push the locking/release profile 22 from the inner (first) position to the outer (second) position. The hanger further is provided with a pair of resiliently moveable locking lugs 30 for engagement with respective abutment surfaces 31 at the ends of the locking/release profile 22 when this is placed in said first position. The structure is best shown in FIG. 7 which shows an enlarged view of the detail B in FIG. 6.

The hanger 21 at each end is also provided with a pair projecting arms 32 for cooperation with corresponding guide members at the ends of the current loading rack (not shown), for guided introduction of the hanger to a well-defined position in the loading rack, in a manner corresponding to that described above in connection with the first embodiment of the holding device.

The design of the locking/release profile 22 is further shown in FIGS. 12A-D. As appears from FIG. 12C, the elongated profile has a generally U-shaped cross-section, and on the inner side of one sidewall 33 there is arranged ten lugs 34 for actuating respective legs of the five clamping springs 23, so that the springs are moved from the released clamping position to the open position when the locking/release profile 22 is moved from the first to the second position. The sidewall 33 is also provided with a pair of guide lugs 35 engaging in associated guide grooves 36 in the hanger 21, for guiding of the profile between the first and the second position. Further, the profile at each end is provided with a guide pin 37 for a respective helical spring 29.

When using the holding device according to this second embodiment the hanger can be placed in the current loading rack before the microscope slides are put in place, and the locking/release profile thereafter is pressed in for locking of the microscope slide. Alternatively, the microscope slides can be loaded into the locking rack before the hanger is introduced therein and the slides thereafter are locked in the hanger.

When the locking/release profile 22 is pressed in, the lugs 34 on the profile release the five clamping springs which will then clamp the present microscope slides against the current abutment members 24 and down against the common plan 26 of the hanger. The profile is retained in the inner position in that the locking lugs 30 on the hanger 21 snap in over the abutment surfaces 31 at each end of the profile.

In order to release the microscope slides, the locking lugs 30 are moved sideways, and the two helical springs 29 then will push the locking/release profile 22 approximately 3 mm outwards until the guide lugs 35 on the profile about against the ends of the guide grooves 36 in the hanger. At the same time the 5×2 lugs 34 on the profile will pull the clamping springs 23 outwards in that the lugs hit a respective spring leg, and the springs will be pressed outwards and open up, so that the microscope slides 12 are released.

The second embodiment of the holding device is designed especially with a view to a simple and user-friendly utilization. Design entails several operationally important advantages. Firstly, the is achieved an individual clamping of the microscope slides and in addition a directional-stabile retention thereof. An additional substantial advantage is that text fields which are usually present at the end of the microscope slides, are not concealed by the locking/release profile when the slide are clamped in the hanger. These text fields will be concealed by the clamping device in the embodiment according to FIGS. 1-3.

The holding device according to the invention is intended for use in a multi-function apparatus for automatic execution of different treatment operations in connection with staining of tissue specimens on microscope slides. FIG. 13 shows a principle drawing of such an apparatus. The apparatus is shown to comprise and loading and preheating station 40 for microscope slides, a number of reagent stations consisting of vessels 41 for staining of tissue specimens on microscope slides, a conveyor 42 for transferring carriers (i.e. holding devices according to the invention) with microscope slides from vessel to vessel in accordance with a treatment program, a means 43 for transfer of the holding devices with microscope slides from the reagent stations to a station 44 for placing of cover glasses on the stained microscope slides, and a succeeding drying station 45 and an unloading station 46. For a further description of this apparatus reference is made to the simultaneously filed international patent application having the title "An apparatus for execution of treatment operations on microscope slides with tissue specimens".

FIG. 14 shows an embodiment of a conveyor 42 for use in the apparatus in FIG. 13. As appears, a holding device 1 with microscope slides 12 is suspended in the conveyor on lifting means 47 arranged to raise and lower the holding device in connection with the transfer by the conveyor of microscope slides from vessel to vessel on the reagent stations. For a further description of the conveyor reference is made to the above-mentioned simultaneously filed patent application.

By means of the holding device according to the invention, a number of substantial advantages are achieved, such as summarized below:

- The holding device reduces entrainment/transfer of reagent liquid to a minimum as compared to the previously known baskets and racks for this purpose.
- The holding device has no frame for localization of microscope slides, like the holder according to WO 94/23326.
- The holding device can be used as a transport device in a staining machine and a cover-slipper without manipulation of the tissue specimen-microscope slide.
- The holding device can be introduced into a transport tray for screening by only releasing the clamping means.
- The holding device can freely receive microscope slides having a width varying within a tolerance region.

The invention claimed is:

1. A holding device for retaining a number of microscope slides with tissue specimens, wherein:
    (i) the surfaces of the microscope slides in retained position are located in a common plane;
    (ii) an elongated hanger having a common plan and a clamping means for releasable clamping of microscope slides in a hanging position with the surfaces in said plane, the microscope slides being clamped at their upper end and by release from the clamping means being free to fall from the hanger because of their own weight; and
    (iii) the clamping means of the hanger comprises a number of clamping springs that each clamp one or more microscope slides, the hanger being arranged to cooperate with an actuating means that can be moved between a first position in which the clamping springs are moved to a clamped position so that they clamp the microscope slides, and a second position in which the clamping springs are moved to an open position in which the microscope slides are released.

2. A holding device according to claim 1, wherein the clamping means is arranged to cooperate with a loading rack having a supporting surface for support of the current microscope slides in said plane, the hanger being able to be introduced into the rack and that the clamping means being able to be actuated so that all microscope slides placed on the supporting surface are clamped in the holding device.

3. A holding device according to claim 2, wherein the hanger at its ends is provided with a pair of projecting arms for cooperation with corresponding guide members at the ends of the loading rack, for guided introduction of the hanger to a defined position in the rack.

4. A holding device according to claim 1, wherein each clamping spring comprises a generally U-shaped wire element having legs with ends, wherein the ends of the spring legs are adapted to actuate a respective pair of microscope slides, so that the microscope slides are clamped against intermediate abutment member members on the hanger.

5. A holding device according to claim 4, wherein the actuating means comprises an elongated locking/release profile having a generally U-shaped cross-section, wherein an inner sidewall of the profile is provided with a number of lugs for actuating the clamping springs so that these are moved from the released clamping position to the open position when the actuating means is moved from the first to the second position.

6. A holding device according to claim 5, wherein said inner sidewall of the profile is also provided with a pair of guide lugs engaging in a associated guide grooves in the hanger, for guiding of the actuating means between the first and the second position.

7. A holding device according to claim 5, wherein the hanger is provided with a pair of helical springs placed at the ends of the locking/release profile and arranged to move the actuating means from the first to the second position.

8. A holding device according to claim 5, wherein the hanger is provided with a pair of locking lugs for engagement with respective abutment surfaces at the ends of the locking/release profile when the actuating means is placed in said first position.

9. A holding device according to claim 4, wherein the abutment members have sidewalls that are inclined upwards and outwards towards the respective microscope slide, so that the ends of the spring legs in the clamped position are pressed against the common plan of the hanger.

10. A holding device according to claim 4, wherein the ends of the legs of the clamping springs are inclined in the direction outwards from the respective microscope slide, so that the springs assist in pressing the microscope slides against the common plan of the hanger.

* * * * *